US008562809B2

(12) United States Patent
Liu et al.

(10) Patent No.: US 8,562,809 B2
(45) Date of Patent: Oct. 22, 2013

(54) CHITOSAN-COATED WIRES FOR BIOSENSING

(75) Inventors: Yi Liu, Bethesda, MD (US); Xiao-Wen Shi, College Park, MD (US); Gregory F. Payne, Hunt Valley, MD (US); W. Lee Meyer, Baltimore, MD (US)

(73) Assignee: University of Maryland, College Park, College Park, MD (US)

( * ) Notice: Subject to any disclaimer, the term of this patent is extended or adjusted under 35 U.S.C. 154(b) by 145 days.

(21) Appl. No.: 13/122,403

(22) PCT Filed: Oct. 2, 2009

(86) PCT No.: PCT/US2009/059372
§ 371 (c)(1),
(2), (4) Date: May 13, 2011

(87) PCT Pub. No.: WO2010/040047
PCT Pub. Date: Apr. 8, 2010

(65) Prior Publication Data
US 2011/0217785 A1 Sep. 8, 2011

Related U.S. Application Data

(60) Provisional application No. 61/238,277, filed on Aug. 31, 2009, provisional application No. 61/102,009, filed on Oct. 2, 2008.

(51) Int. Cl.
*C25D 9/02* (2006.01)
(52) U.S. Cl.
USPC .......................................... 205/229; 205/317
(58) Field of Classification Search
USPC ................................. 205/229, 317
See application file for complete search history.

(56) References Cited

U.S. PATENT DOCUMENTS

| 7,138,373 | B2 | 11/2006 | Chen et al. |
| 7,375,404 | B2 | 5/2008 | Park et al. |
| 2006/0102486 | A1* | 5/2006 | Bentley et al. ................. 205/118 |
| 2007/0068824 | A1* | 3/2007 | Payne et al. ................... 205/317 |
| 2007/0172821 | A1 | 7/2007 | Wu et al. |

OTHER PUBLICATIONS

Luo et al., "A Glucose Biosensor Based on Chitosan-Glucose Oxidase-Gold Nanoparticles Biocomposite Formed by One-Step Electrodeposition" Anal. Biochem. 334, pp. 284-289 (2004).*

(Continued)

*Primary Examiner* — Harry D Wilskins, III
*Assistant Examiner* — Bryan D. Ripa
(74) *Attorney, Agent, or Firm* — Hultquist, PLLC; Steven J. Hultquist

(57) ABSTRACT

A method of forming a bioelectronic device including a protein on an electrically conductive substrate, by electrodepositing aminopolysaccharide chitosan on the substrate while applying a cathodic voltage to the substrate, to form an aminopolysaccharide chitosan film thereon, applying an anodic voltage to the substrate in the presence of NaCl to activate the aminopolysaccharide chitosan film so that it is reactive with protein. The method also optionally includes reacting the aminopolysaccharide film, after activation thereof, with the protein, so that the protein assembles on and is coupled to the substrate, thereby forming a bioelectronic device. The protein can include single or multiple protein species, and including biosensing proteins. Additional methods include biosensing of electrochemically active compounds either present in a sample or generated during a biological recognition event and devices useful in such methods. The resulting devices are useful as sensors in hand-held devices, textiles, garments and the like.

10 Claims, 9 Drawing Sheets

(56) References Cited

OTHER PUBLICATIONS

Kang et al., "A Novel Glucose Biosensor Based on Immobilization of Glucose Oxidase in Chitosan on a Glassy Carbon Electrode Modified with Gold-Platinum Alloy Nanoparticles/Multiwall Carbon Nanotubes" Anal. Biochem. 369, pp. 71-79 (2007).*
Xi, F., et al., "One-step construction of biosensor based on chitosan-ionic liquid-horseradish peroxidase biocomposite formed by electrodeposition", "Biosensors and Bioelectronics", Mar. 30, 2008, pp. 29-34, vol. 24.
Yi, H., et al, "Biofabrication with Chitosan", "Biomacromolecules", Sep. 3, 2005, pp. 2881-2894, vol. 6, No. 6.
Zhou, Q., et al., "Electrodeposition of Carbon Nanotubes-Chitosan-Glucose Oxidase Biosensing Composite Films Triggered by Reduction of p-Benzoquinone or $H_2O_2$", "J. Phys. Chem.", Sep. 6, 2007, pp. 11276-11284, vol. 111.
Zou, Y., et al., "Glucose biosensor based on electrodeposition of platinum nanoparticles onto carbon nanotubes and immobilizing enzyme with chitosan-$SiO_2$ sol—gel", "Biosensors and Bioelectronics", Oct. 25, 2007, pp. 1010-1016, vol. 23.
Abouraddy, A., et al., "Towards multimaterial multifunctional fibres that see, hear, sense and communicate", "Nature Materials", May 2007, pp. 336-347, vol. 6.
Arts, I., et al., "Catechin Contents of Foods Commonly Consumed in the Netherlands.1. Fruits, Vegetables, Staple Foods, and Processed Foods", "J. Agric. Food Chem.", Apr. 25, 2000, pp. 1746-1751, vol. 48.
Arts, I., et al., "Catechin Contents of Foods Commonly Consumed in the Netherlands. 2. Tea, Wine, Fruit Juices, and Chocolate Milk", "J. Agric. Food Chem.", Apr. 25, 2000, pp. 1752-1757, vol. 48.
Bai, Y., et al., "Choline biosensors based on a bi-electrocatalytic property of $MnO_2$ nanoparticles modified electrodes to $H_2O_2$", "Electrochemistry Communications", Aug. 19, 2007, pp. 2611-2616, vol. 9.
Bardetsky, D., et al., "Electrochemical preparation of composite films containing cationic polyelectrolytes and cobalt hydroxide", "Surface Engineering", Apr. 2005, pp. 125-130, vol. 21, No. 2.
Casagrande, T., et al., "Electrodeposition of composite materials containing functionalized carbon nanotubes", "Materials Chemistry and Physics", May 2, 2008, pp. 42-49, vol. 111.
Castillo, J., et al., "Biosensors for life quality Design, development and applications", "Sensors and Actuators B", Jun. 7, 2004, pp. 179-194, vol. 102.
Coyle, S., et al., "Smart Nanotextiles: A Review of Materials and Applications", "MRS Bulletin", May 2007, pp. 434-442, vol. 32.
Dalluge, J., et al., "Determination of tea catechins", "Journal of Chromatography A", Jun. 2000, pp. 411-424, vol. 881.
Desai, K., et al., "Morphological and Surface Properties of Electrospun Chitosan Nanofibers", "Biomacromolecules", Jan. 17, 2008, pp. 1000-1006, vol. 9.
Devaux, E., et al., "Processing and characterization of conductive yarns by coating or bulk treatment for smart textile applications", "Transactions of the Institute of Measurement and Control", Aug. 2007, pp. 355-376, vol. 29, No. 3/4.
Du, Y. et al., "A simple method to fabricate a chitosan-gold nanoparticles film and its application in glucose biosensor", "Bioelectrochemistry", May 16, 2006, pp. 342-347, vol. 70.
Epstein, J., et al., "Fluorescence-based fibre optic arrays: a universal platform for sensing", "Chem. Soc. Rev.", Apr. 14, 2003, pp. 203-214, vol. 32.
Grandfield, K., et al., "Electrophoretic deposition of composite hydroxyapatite-silica-chitosan coatings", "Materials Characterization 2008", Dec. 6, 2006, pp. 61-67, vol. 59, No. 1.
Hamedi, M., et al., "Towards woven logic from organic electronic fibres", "Nature Materials", Apr. 4, 2007, pp. 357-362, vol. 6.
Hao, C., et al., "Biocompatible Conductive Architecture of Carbon Nanofiber-Doped Chitosan Prepared with Controllable Electrodeposition for Cytosensing", "Analytical Chemistry", Jun. 15, 2007, pp. 4442-4447, vol. 79.

Heller, A., et al., "Electrochemical Glucose Sensors and Their Applications in Diabetes Management", "Chem. Rev.", May 9, 2008, pp. 2482-2505, vol. 108.
Huang, C., et al., "A wearable yarn-based piezo-resistive sensor", "Sensors and Actuators A", Nov. 1, 2007, pp. 396-403, vol. 141.
Jung, S., et al., "Point-of-care temperature and respiration monitoring sensors for smart fabric applications", "Smart Mater. Struct.", Nov. 2, 2006, pp. 1872-1876, vol. 15.
Junker, H., et al., "Gesture spotting with body-worn inertial sensors to detect user activities", "Pattern Recognition", Nov. 23, 2007, pp. 2010-2024, vol. 41.
Kang, X., et al., "A novel glucose biosensor based on immobilization of glucose oxidase in chitosan on a glassy carbon electrode modified with gold-platinum alloy nanoparticles/multiwall carbon nanotubes", "Analytical Biochemistry", Jul. 7, 2007, pp. 71-79, vol. 369.
Klossner, R., et al., "Correlation of Chitosan's Rheological Properties and Its Ability to Electrospin", "Biomacromolecules", Sep. 12, 2008, pp. 2947-2953, vol. 9.
Ko, S., et al., "A novel FRET-based optical fiber biosensor for rapid detection of *Salmonella* typhimurium", "Biosensors and Bioelectronics", Jul. 22, 2005, pp. 1283-1290, vol. 21.
Kriegel, C., et al., "Fabrication, Functionalization, and Application of Electrospun Biopolymer Nanofibers", "Critical Reviews in Food Science and Nutrition", Aug. 28, 2008, pp. 775-797, vol. 48, No. 8.
Leung, A., et al., "A review of fiber-optic biosensors", "Sensors and Actuators B", Mar. 15, 2007, pp. 688-703, vol. 125.
Leung, A., et al., "Label-free detection of DNA hybridization using gold-coated tapered fiber optic biosensors (TFOBS) in a flow cell at 1310 nm and 1550 nm", "Sensors and Actuators B", Jan. 8, 2008, pp. 640-645, vol. 131.
Liu, Y., et al., "Functionalization of cotton with carbon nanotubes", "J. Mater. Chem", Jun. 16, 2008, pp. 3454-3460, vol. 18.
Liu, Y., et al., "Chitosan-Coated Electrodes for Bimodal Sensing: Selective Post-Electrode Film Reaction for Spectroelectrochemical Analysis", "Langmuir", Jun. 12, 2008, pp. 7223-7231, vol. 24.
Lu, Y., et al., "Enzyme-functionalized gold nanowires for the fabrication of biosensors", "Bioelectrochemistry", Jun. 14, 2007, pp. 211-216, vol. 71.
Luo, X., et al., "A glucose biosensor based on chitosan-glucose oxidase-gold nanoparticles biocomposite formed by one-step electrodeposition", "Analytical Biochemistry", Aug. 24, 2004, pp. 284-289, vol. 334.
Luo, X., et al., "Electrochemically deposited chitosan hydrogel for horseradish peroxidase immobilization through gold nanoparticles self-assembly", "Biosensors and Bioelectronics", Sep. 11, 2004, pp. 190-196, vol. 21.
Manesh, K., et al., "A novel glucose biosensor based on immobilization of glucose oxidase into multiwall carbon nanotubes-polyelectrolyte-loaded electrospun nanofibrous membrane", "Biosensors and Bioelectronics", Aug. 30, 2007, pp. 771-779, vol. 23.
Pang, X., et al., "Electrodeposition of composite hydroxyapatite-chitosan films", "Materials Chemistry and Physics", Dec. 15, 2005, pp. 245-251, vol. 94.
Pang, X., et al., "Electrophoretic deposition of composite hydroxyapatite-chitosan coatings", "Materials Characterization", May 23, 2005, pp. 339-348, vol. 58.
Pang, X., et al., "Electrodeposition of hydroxyapatite-silver-chitosan nanocomposite coatings", "Surface & Coatings Technology", Feb. 2008, pp. 3815-3821, vol. 202.
Rijal, K., et al., "Detection of pathogen *Escherichia coli* O157:H7 At 70 cells/mL using antibody-immobilized biconical tapered fiber sensors", "Biosensors and Bioelectronics", Mar. 17, 2005, pp. 871-880, vol. 21.
Schiffman, J., et al., "Cross-Linking Chitosan Nanofibers", "Biomacromolecules", Dec. 30, 2006, pp. 594-601, vol. 8.
Schiffman, J., et al., "A Review: Electrospinning of Biopolymer Nanofibers and their Applications", "Polymer Reviews", May 2, 2008, pp. 317-352, vol. 48.
Shi, Q., et al., "The immobilization of proteins on biodegradable polymer fibers via click chemistry", "Biomaterials", Nov. 26, 2007, pp. 1118-1126, vol. 29.

(56) References Cited

OTHER PUBLICATIONS

Shi, X., et al., "Reagentless Protein Assembly Triggered by Localized Electrical Signals", "Advanced Materials", Dec. 15, 2008, pp. 984-988, vol. 21, No. 9.

Shi, X., et al., "Chitosan Fibers: Versatile Platform for Nickel-Mediated Protein Assembly", "Biomacromolecules", Apr. 10, 2008, pp. 1417-1423, vol. 9.

Tan, X., et al., "Glucose biosensor based on glucose oxidase immobilized in solgel chitosan/silica hybrid composite film on Prussian blue modified glass carbon electrode", "Anal Bioanal Chem", Jan. 19, 2005, pp. 500-507, vol. 381.

Wallace, G., et al., "Conducting polymers—bridging the bionic interface", "Soft Matter", Apr. 11, 2007, pp. 665-671, vol. 3.

Wang, J., "Electrochemical Glucose Biosensors", "Chem. Rev.", Dec. 23, 2007, pp. 814-825, vol. 108.

Wolfbeis, O., "Fiber-Optic Chemical Sensors and Biosensors", "Analytical Chemistry", May 8, 2008, pp. 4269-4283, vol. 80.

Wu, L., et al., "Voltage-Dependent Assembly of the Polysaccharide Chitosan onto an Electrode Surface", "Langmuir", Sep. 21, 2002, pp. 8620-8625, vol. 18.

Wu, L., et al., "Spatially Selective Deposition of a Reactive Polysaccharide Layer onto a Patterned Template", "Langmuir", Jan. 4, 2003, pp. 519-524, vol. 19.

Wu, L., et al., "Biometric Pattern Transfer", "Advanced Functional Materials", Feb. 2005, pp. 189-195, vol. 15, No. 2.

Wu, L., et al., "Mimicking Biological Phenol Reaction Cascades to Confer Mechanical Function", "Advanced Functional Materials", Aug. 21, 2006, pp. 1967-1974, vol. 16.

Wu, B., et al., "Amperometric glucose biosensor based on layer-by-layer assembly of multilayer films composed of chitosan, gold nanoparticles and glucose oxidase modified Pt electrode", "Biosensors and Bioelectronics", May 3, 2006, pp. 838-844, vol. 22.

* cited by examiner (a) (b) (c)

(a) (b)

CHITOSAN-COATED WIRES FOR BIOSENSING

CROSS REFERENCE TO RELATED APPLICATIONS

This application is a U.S. national phase application under the provisions of 35 U.S.C. §371 of International Patent Application No. PCT/US09/59372 filed Oct. 2, 2009, and published on Apr. 8, 2010 as International Publication No. WO 2010/040047, which in turn claims the benefit of U.S. Provisional Patent Application No. 61/102,009 filed Oct. 2, 2008 in the names of Xiao-Wen Shi, Yi Liu and Gregory F. Payne for "Electrical Signal Guided Protein Assembly" and further claims the benefit of U.S. Provisional Patent Application No. 61/238,277 filed Aug. 31, 2009 in the names of Yi Liu, Xiao-Wen Shi, Gregory F. Payne and W. Lee Meyer for "Chitosan-Coated Wires for Biosensing." The disclosures of such international patent application and U.S. priority patent application are hereby incorporated herein by reference in their respective entireties, for all purposes.

GOVERNMENT RIGHTS IN INVENTION

This invention was made with government support under Grant No. CBET-0650650 and Grant No. EFRI-0735987, awarded by the National Science Foundation and Grant No. W91B9480520121 awarded by the Department of Defense. The Government has certain rights in this invention.

FIELD OF THE INVENTION

The present invention relates to a system and method for utilizing electrical signals to effect protein assembly, and devices produced thereby. Particularly, methods of making and using devices containing chitosan-coated electrodes are provided. The devices produced by the methods described herein provide convenient biosensing platforms that couple biological capabilities for selective detection with electronics technology for signal transduction.

DESCRIPTION OF THE RELATED ART

Electronics and biology provide unique capabilities for sensing, and these capabilities are increasingly being employed for analysis outside the laboratory. Electronics offer an array of sensors to detect physical and mechanical conditions, and electronics offer extensive signal processing capabilities. Recent investigations aim to incorporate the sensing and transduction capabilities of electronics into wearable instrumentation (Junker, H. et al., *PatternRecognit.*2008, 41, 2010-2024.) or smart textiles. (Coyle, S., et al. *MRS-Bull.*2007, 32, 434-442; Abouraddy, A. F., et al. *Nat.Mater.* 2007, 6, 336-47; Hamedi, M., et al. *Nat.Mater.*2007, 6, 357-62.) These smart textiles can monitor the wearer's actions, wirelessly communicate this information, and potentially even guide motion. Smart textiles that offer such physical and mechanical sensing capabilities are expected to provide important benefits (e.g., to detect that a house-bound person has fallen or to assess danger to a firefighter).(Huang, C. T., et al. *Sens.Actuator,*2008, 141, 396-403; Jung, S., et al. *Smart-Mater.Struct.*2006, 15, 1872-1876; Devaux, E., et al., *Trans.Inst.Meas.Control* 2007, 29, 355-376; Liu, Y. Y., et al. *J.Mater.Chem.* 2008, 18, 3454-3460.) Such textiles would be even smarter if they could detect and report chemical and biochemical information. (Wallace, G., et al. *SoftMatter* 2007, 3, 665-671.)

Biological recognition elements (e.g., nucleic acids, enzymes and antibodies) permit the selective detection of chemical and biochemical information, and these elements are extensively employed for laboratory analysis (e.g., microarrays and immunoassays). There is a growing interest in creating platforms that enable these biological recognition elements to be employed outside the laboratory. Several groups are advocating the use of fibers and fabrics as platforms for biosensing in the field. For instance, fiber optics are commonly considered for chemical and biochemical sensing because optical fibers offer considerable signal transduction capabilities. (Wolfbeis, O. S., et al. *Anal.Chem.*2008, 80, 4269-83; Leung, A., et al. *Sens.Actuators,* 2007, 125, 688-703; Leung, A., et al. *Sens.Actuators,* 2008, 131, 640-645; Ko, S. H., et al. *Biosens.Bioelectron.* 2006, 21, 1283-1290; Rijal, K., et al. *Biosens.Bioelectron.* 2005, 21, 871-880; Epstein, J. R., et al. *Chem.Soc.Rev.* 2003, 32, 203-14.) One limitation of fiber optic systems is that the incorporation of the biological sensing element is not always simple or benign. Alternatively, polymer based fibers (and nanofibers) and fabrics (Schiffman, J. D., et al. *Biomacromolecules* 2007, 8, 594-601; Schiffman, J. D., et al. *Polym.Rev.* 2008, 48, 317-352; Klossner, R. R., et al. *Biomacromolecules* 2008, 9, 2947-53; Desai, K., et al. *Biomacromolecules* 2008, 9, 1000-6; Kriegel, C., et al. *Crit.ReV.FoodSci.Nutr.* 2008, 48, 775-797) are being examined as a platform for biosensing. (Shi, X. W., et al. *Biomacromolecules* 2008, 9, 1417-23; Shi, Q., et al. *Biomaterials* 2008, 29, 1118-1126). In many cases, polymeric fibers are more readily biofunctionalized although signal transduction with polymers is not as straightforward when compared to optical fibers.

There is great interest in coupling the capabilities of electronics with the molecular recognition properties of biology to generate hand-held devices that can diagnose diseases at the point-of-care, analyze environmental samples in the field, and assess food safety from the farm to the table. A key challenge is the integration of the labile biological recognition elements (e.g., proteins) at specific device addresses or locations.

There therefore remains a need in the art for development of a biosensing platform that can be readily biofunctionalized and that allows the transduction of biological recognition into convenient electrical signals. The present invention provides such a platform and methods of making and using the same.

SUMMARY OF THE INVENTION

In one aspect, the invention relates to a method of forming a bioelectronic device including a protein on an electrically conductive substrate, comprising:
  electrodepositing aminopolysaccharide chitosan on the substrate while applying a cathodic voltage to the substrate, to form an aminopolysaccharide chitosan film thereon;
  applying an anodic voltage to the substrate in the presence of NaCl to activate the aminopolysaccharide chitosan film so that it is reactive with protein; and
  reacting the aminopolysaccharide film, after activation thereof, with the protein, so that the protein assembles on and is coupled to the substrate, thereby forming said bioelectronic device.

Another aspect of the invention relates to a method of forming an electrically conductive substrate adapted for assembly of protein species thereon, said method comprising:

electrodepositing aminopolysaccharide chitosan on the substrate while applying a cathodic voltage to the substrate, to form an aminopolysaccharide chitosan film thereon; and applying an anodic voltage to the substrate in the presence of NaCl to activate the aminopolysaccharide chitosan film so that it is reactive with protein.

The invention relates in a further aspect to a bioelectronic device, e.g., a hand-held device, comprising:

an electrically conductive substrate;

an electrodeposited aminopolysaccharide chitosan film on the substrate; and protein conjugated to the electrodeposited aminopolysaccharide chitosan film.

The invention relates in a further aspect to a bioelectronic precursor device, comprising:

an electrically conductive substrate; and an electrodeposited aminopolysaccharide chitosan film on the substrate, wherein said film is adapted to react with and conjugate a protein.

In another aspect the invention relates to a method of detecting the presence of a protein in a sample comprising the steps of:

contacting the sample with a bioelectronic device, comprising: i) an electrically conductive substrate; and ii) an electrodeposited aminopolysaccharide chitosan film on the substrate, wherein said film is reactive with a protein under conditions sufficient to react the film with the protein;

detecting the presence or absence of the reacted protein.

In a still further aspect the invention relates to a method of transducing enzyme substrate recognition into an electrical signal comprising the steps of:

obtaining a bioelectronic device, comprising: i) an electrically conductive substrate; and ii) an electrodeposited aminopolysaccharide chitosan film on the substrate, wherein said film is conjugated with an enzyme;

contacting the bioelectronic device with a substrate-containing sample, wherein the substrate is reactive with the enzyme of the bioelectronic device under conditions sufficient to react the substrate and the enzyme;

detecting the anodic current, wherein a change in anodic current is an electrical signal indicative of enzyme substrate recognition.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
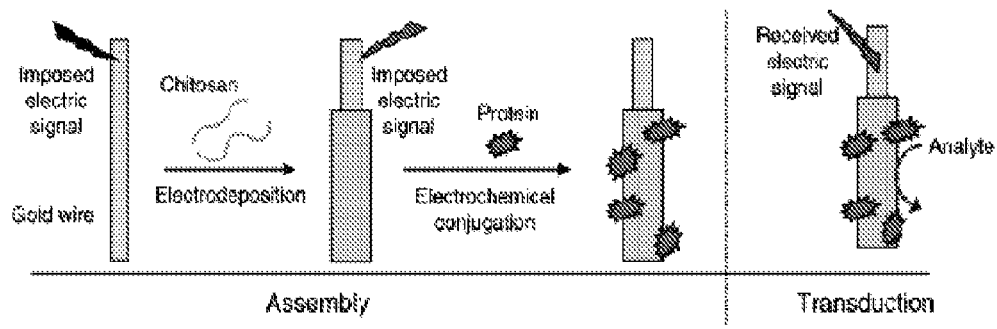
FIG. 1 is an illustration of the scheme of the invention, where gold wires are biofunctionalized using cathodic signals to electrodeposit chitosan and anodic signals to activate the chitosan for protein assembly.

The present invention is based on the discovery of a simple, safe and generic approach for assembling proteins in response to electrode-imposed electrical signals and for biofunctionalization of the initial platform. This approach relies on the aminopolysaccharide chitosan that can be electrodeposited in response to cathodic signals and then electrochemically activated by anodic signals. The electodeposited and electroactivated chitosan films react with proteins to assemble them with spatial-selectivity and quantitative-control. The present inventors have found that the assembled proteins retain their native structure and biological functions. The resulting devices are useful in methods of biosensing using the conjugated proteins. Furthermore, the present invention provides additional devices for and methods of biosensing, where the biosensing platforms contain elements permeable to small molecules, allowing detection of electrochemically active compounds, whether present in the solution or generated during a biological recognition event, such as enzyme substrate recognition.

The inventive methodology for on-demand biofunctionalization of individual electrode addresses, as discussed more fully hereinafter, provides a reliable capability for assembling proteins for multiplexed analysis.

In one aspect, the invention relates to a method of forming a bioelectronic device including a protein on an electrically conductive substrate, comprising:
   electrodepositing aminopolysaccharide chitosan on the substrate while applying a cathodic voltage to the substrate, to form an aminopolysaccharide chitosan film thereon;
   applying an anodic voltage to the substrate in the presence of NaCl to activate the aminopolysaccharide chitosan film so that it is reactive with protein; and
   reacting the aminopolysaccharide film, after activation thereof, with the protein, so that the protein assembles on and is coupled to the substrate, thereby forming said bioelectronic device.

In a specific embodiment, the substrate comprises a multiplexing chip having a multiplicity of electrode addresses, wherein the electrode addresses independently have protein assembled thereon and coupled thereto. The multiplicity of electrode addresses can have different protein species assembled thereon and coupled thereto. The protein can comprise one or more types of biosensor protein species.

Another aspect of the invention relates to a method of forming an electrically conductive substrate adapted for assembly of protein species thereon, said method comprising:
   electrodepositing aminopolysaccharide chitosan on the substrate while applying a cathodic voltage to the substrate, to form an aminopolysaccharide chitosan film thereon; and
   applying an anodic voltage to the substrate in the presence of NaCl to activate the aminopolysaccharide chitosan film so that it is reactive with protein.

The invention relates in a further aspect to a bioelectronic device, e.g., a hand-held device, comprising:
   an electrically conductive substrate;
   an electrodeposited aminopolysaccharide chitosan film on the substrate; and
   protein conjugated to the electrodeposited aminopolysaccharide chitosan film.

The invention relates in a further aspect to a bioelectronic precursor device, comprising:
   an electrically conductive substrate; and
   an electrodeposited aminopolysaccharide chitosan film on the substrate, wherein said film is adapted to react with and conjugate a protein.

Figure 2:
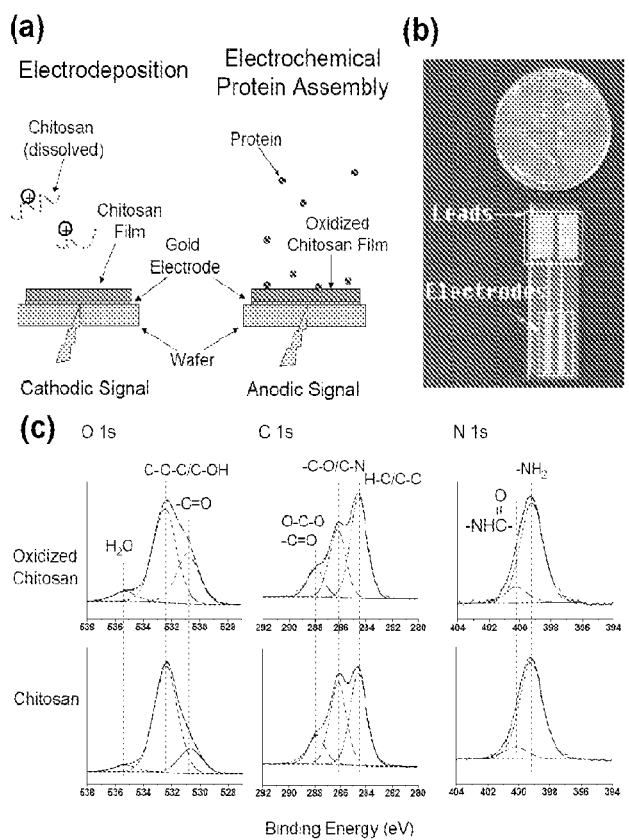
FIG. 2 relates to electro-addressing of proteins, including (a) a schematic illustration of a two-step approach in which a cathodic signal is used to electrodeposit an aminopolysaccharide chitosan, and an anodic signal is used to electrochemically activate the chitosan film for protein assembly; (b) a chip with two electrically-independent gold electrodes (1 mm×8 mm) patterned onto silicon; and (c) high-resolution XPS spectra of a control chitosan film and a chitosan film oxidized at 0.9 V to achieve a charge transfer of 80 C/m$^2$.

The invention in one aspect relates to a two-step approach for enlisting electrical signals for protein assembly. This approach is illustrated in FIG. 2(a) and relies on the unique physical and chemical properties of the aminopolysaccharide chitosan.

In another aspect the invention relates to a method of detecting the presence of a protein in a sample comprising the steps of:
    contacting the sample with a bioelectronic device, comprising: i) an electrically conductive substrate; and ii) an electrodeposited aminopolysaccharide chitosan film on the substrate, wherein said film is reactive with a protein under conditions sufficient to react the film with the protein;
    detecting the presence or absence of the reacted protein.

In a still further aspect the invention relates to a method of transducing enzyme substrate recognition into an electrical signal comprising the steps of:
    obtaining a bioelectronic device, comprising: i) an electrically conductive substrate; and ii) an electrodeposited aminopolysaccharide chitosan film on the substrate, wherein said film is conjugated with an enzyme;
    contacting the bioelectronic device with a substrate-containing sample, wherein the substrate is reactive with the enzyme of the bioelectronic device under conditions sufficient to react the substrate and the enzyme;
    detecting the anodic current, wherein a change in anodic current is an electrical signal indicative of enzyme substrate recognition.

Chitosan is a unique interface material that allows conducting wires to be biofunctionalized through simple electrical signals. Specifically, in the claimed invention, cathodic signals are used to direct chitosan to electrodeposit onto gold wires and anodic signals are used to conjugate proteins to the chitosan-coated wire. In addition, the chitosan-coating is permeable to small molecules which allows for the electrical detection of electrochemically-active compounds that are either present in the external environment or generated by a biofunctionalized chitosan coating. The capabilities for biofunctionalization and transduction are exemplified herein by the detection of glucose by chitosan-coated wires functionalized with the enzyme glucose oxidase. Chitosan-coated wires (or alternatively conducting chitosan fibers) are a simple platform that may permit multiplexed biosensing outside the laboratory.

In the methods and devices of the invention, the electrically conductive substrate may comprise an electrode, e.g., a gold electrode, on a silicon chip. The electrically conductive substrate of the invention may comprise any noble or non-noble metal, including, but not limited to: gold, copper, ruthenium, rhodium, palladium, silver, osmium, iridium, and platinum. In another aspect the electrically conductive substrate of the invention comprises graphene. In various aspects, the electrically conductive substrate of the invention is in any form effective for conjugation, as described. Such forms include, but are not limited to a wire, a panel, mesh, a scaffold, and the like.

The protein conjugated to the chitosan film on the substrate can be of any suitable type, such as avidin, an immunoglobulin-binding protein such as protein G, RFP, GFP, or other suitable protein(s).

The substrate may comprise a multiplexing chip having a multiplicity of electrode addresses, wherein the electrode addresses independently have protein conjugated thereto, e.g., different protein species including biosensor protein species.

Electrodeposition of Chitosan

As illustrated in FIG. 1, the present invention provides use of the amino polysaccharide chitosan to serve as the interface between the protein-based recognition element and a metal wire. Importantly chitosan allows proteins to be assembled in response to imposed electrical signals without the need for reactive reagents or harsh conditions. (Shi, X. W., et al. *Adv. Mater.* 2009, 21, 984-988.) Thus, biofunctionalization is simple, safe, and rapid. Further, the chitosan-coating is permeable to small molecules and allows the detection of electrochemically active compounds that are either present in the solution or generated during the biological recognition event. Thus, chitosan-coated electrodes can transduce chemical and biological information into convenient electrical signals.

Chitosan electrodeposition has been extensively studied on planar electrode surfaces (Wu, L. Q., et al. *Langmuir* 2002, 18, 8620-8625; Wu, L. -Q., et al. *Langmuir* 2003, 19, 519-524; Yi, H., et al. *Biomacromolecules* 2005, 6, 2881-94; Casagrande, T., et al. *Mater.Chem.Phys.* 2008, 111, 42-49; Pang, X., et al. *Surf Coat.Technol.* 2008, 202, 3815-3821; Bardetsky, D., et al. *Surf.Eng.* 2005, 21, 125-130; Hao, C., et al. *Anal.Chem.* 2007, 79, 4442-7) and chitosan electrodeposition on wires and wire meshes has been demonstrated. (Pang, X., et al. *Mater.Chem.Phys.* 2005, 94, 245-251; Grandfield, K., et al. *Mater.Charact.* 2008, 59, 61-67; Pang, X., et al. *Mater.Charact.* 2007, 58, 339-348.)

In a first step of generating devices of the invention, chitosan is electrodeposited as a thin film onto a cathode surface. Mechanistically, cathodic reactions create a localized region of high pH that induces electrodeposition due to chitosan's pH-responsive film-forming properties. Mechanistically, chitosan electrodeposition occurs because the locally high pH at the cathode surface induces a sol-gel transition of the pH-responsive chitosan (chitosan is soluble at pH below it spKa of 6.0-6.5). Once deposited and rinsed, the chitosan film is stable on the electrode in the absence of an applied potential provided the pH is retained above about 6.3(however, the film re-dissolves at lower pHs).

The second step of generating devices of the invention comprises electrochemical activation of the deposited chitosan film. Activation is achieved by biasing the underlying electrode to an anodic voltage to generate a diffusible mediator that can partially oxidize chitosan to generate substituents on this polysaccharide that are reactive toward proteins.

Electrodeposition and activation of chitosan films for protein assembly can be carried out under any suitable conditions, as will be readily determinable for specific implementations of the invention, based on the disclosure herein. For example, chitosan can be initially electrodeposited onto gold electrodes patterned onto silicon chips, as shown in FIG. 2(b).

Electrodeposition in an illustrative embodiment can be achieved by partially immersing the chips in a chitosan solution (e.g., 0.9% chitosan, at a pH of 5.6) and applying a cathodic voltage (for example, at 4 A/m$^2$ for 15 seconds) to the specific electrode.

Figure 8:
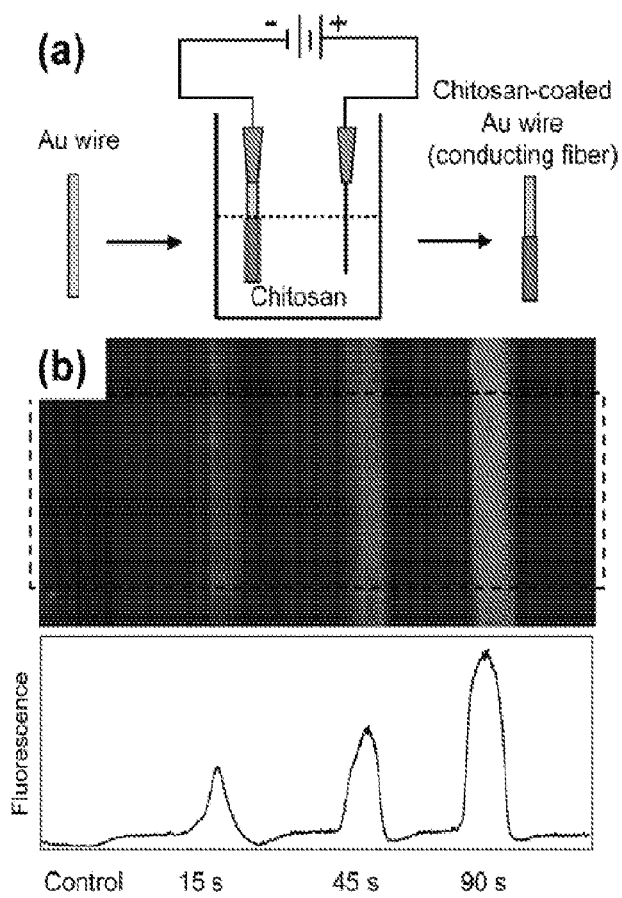
FIG. 8 relates to electrodeposition of fluorescently labeled chitosan onto gold wires. (a) Schematic illustrating chitosan electrodeposition onto a gold wire in response to cathodic signals. (b) Fluorescence photomicrographs of labeled-chitosan deposited onto gold wires. Deposition was achieved by applying a cathodic voltage at a constant current density (12.6 A/m$^2$) for 15, 45, and 90 s. The control is gold wire immersed in chitosan solution for 90 s in the absence of an applied voltage.

The schematic in FIG. 8(a) provides a further illustrative embodiment where electrodeposition is performed by partially immersing the wires in a chitosan solution (1.0% chitosan; pH of 5.6) and applying a cathodic voltage to achieve a constant current density (12.6 A/m$^2$) for a short time (15-90 s). To facilitate visualization, deposition was performed using fluorescein-labeled chitosan. (Example 6) After deposition, the wires were rinsed and imaged using a fluorescence microscope. The control wire shown at the left in FIG. 8(b) was immersed in the labeled-chitosan solution for 90 s, however, no voltage was applied. The image and image analysis for this control show little fluorescence, indicating that nonspecific adhesion of chitosan to the gold wire is minimal. The fluorescence on the remaining wires was observed to increase as the deposition time was increased. These results confirm that chitosan electrodeposition can be performed on gold wires. The present inventors also observed that chitosan can be effectively electrodeposited onto copper wires.

Protein Deposition

Chitosan films can be activated for protein assembly by anodic oxidation of the underlying electrode in the presence of NaCl. (Shi, X.-W., et al. *Adv.Mater.* 2009, 21, 984-988.) It has been found that protein assembly does not occur if anodic activation is performed in the absence of NaCl. (Example 3) Such result is consistent with chitosan activation by HOCl or OCl$^-$ species.

In an illustrative embodiment, after electrodeposition of chitosan, the chips are rinsed and the chitosan films are chemically activated by immersing them in phosphate buffer (0.1 M, pH 7) containing NaCl (0.1 M), and biasing the underlying electrode to an anodic potential of (0.9 V) for short times (<1 min). After rinsing the chips with the activated chitosan films, target proteins are assembled by incubating with the protein-containing solutions for 0.5-1 hr.

It has also been empirically determined that proteins do not assemble to activated chitosan films that are treated with the reducing agent NaBH$_4$ (0.2 mg/ml) for 1 hr prior to protein assembly. This finding is consistent with the presence of aldehydes as activated substituents on the chitosan films.

Direct spectroscopic evidence that anodic oxidation chemically alters the chitosan films is provided by X-ray photoelectron spectroscopy (XPS). This was analytically shown by first electrodepositing chitosan films onto two electrode addresses of the chip shown in FIG. 2(b). The chitosan film on one electrode was anodically oxidized by biasing the underlying electrode (0.9 V) to achieve a charge transfer of 80 C/m$^2$ (approximately 10 sec). The second electrode served as an unoxidized control. After activation, the chip was immersed in 0.1 M HCl for 30 min to partially dissolve unreacted chitosan and expose regions of the films that were closer to the electrode surface. The films were then neutralized with 1 M NaOH for 30 minutes, washed and then analyzed by XPS.

The resulting spectra are shown in FIG. 2(c). The left-most spectra in FIG. 2(c) compare the O 1 s regions for activated (upper spectrum) and control chitosan films. The spectra in the O 1 s region is fit to 3 peaks corresponding to C—O at ~532.5 eV, C═O at ~530.8 eV and physisorbed H$_2$O at ~535.3 eV. The anodically activated chitosan film had an increased C═O peak relative to C—O peak when compared to the control film, which is consistent with oxidation of the chitosan film to generate aldehyde substituents. The middle spectra in FIG. 2(c) show the C 1 s region which is fitted to three peaks at 287.9, 286.2, and 284.6 eV corresponding to C═O/O—C—O, C—O/C—N and C—H/C—C, respectively. The C 1 s spectra show an increase in the ratio of C═O/O—C—O to C—O/C—N peaks for the oxidized chitosan, which is consistent with results from the O 1 s spectra. The right-most spectra in FIG. 2(c) are for the N 1 s region which is fitted to two peaks with a fixed separation of 1 eV at 399.2 eV and 400.2 eV, corresponding to the amine and amide N of chitosan, respectively. The spectra for the oxidized and control films were qualitatively similar in the N 1 s region.

The observed spectral differences in FIG. 2(c) were consistent with two chitosan oxidation mechanisms: (i) cleavage of primary amine and C2-C3 linkage of glucosamine residues to generate a residue with two aldehyde substituents, and (ii) oxidation at the C6 primary hydroxyl to yield aldehyde and carboxylate functionalites. While differences in XPS spectra cannot discern between these two oxidation mechanisms (or alternative mechanisms), they are consistent with chemical changes to the polysaccharide structure and the generation of carbonyl residues (aldehydes).

Controlled assembly of proteins onto electrodeposited and electroactivated chitosan films in accordance with the invention can be carried out in any suitable manner. In an illustrative embodiment, a chip of a type shown in FIG. 3(a) is used for the controlled assembly of proteins onto electrodeposited and electroactivated chitosan films. This chip possessed 6 electrically independent gold electrode addresses (250 μm wide gold lines spaced 250 μm apart). Chitosan was first electrodeposited onto these electrode addresses using the conditions described above, rinsed, and then immersed in the activation solution (0.1 M phosphate buffer with 0.1 M NaCl). To electrochemically activate the chitosan film at an individual address, the underlying gold electrode was biased (0.9 V) to serve as the working electrode, while a Pt wire was used as the counter electrode and Ag/AgCl was used as the reference electrode. The extent of film activation at each electrode address was varied by varying the time that the anodic voltage was applied. The entire chip remained immersed in the activation solution during the sequence of film-activation steps, and the process of activating all 6 electrode addresses took approximately 2 minutes.

Two proteins important for biosensing applications were used to demonstrate controlled assembly onto the electrochemically activated chitosan films. As indicated in FIG. 3(b), avidin was assembled by immersing the chip with the activated chitosan films into a solution (4 ml) containing avidin (0.15 μM) for 1 hr. After assembling the avidin, the chip was rinsed and then immersed in a solution (4 ml) containing fluorescently-labeled biotin (0.3 μM) for 0.5 hr. The fluorescence photomicrograph in FIG. 3(b) shows a progressive increase in the fluorescence for the set of electrode addresses.

The second protein assembled onto the electrochemically activated chitosan films was the streptococcal Fc-binding protein, Protein G. The conditions described above were used to electrodeposit and electrochemically activate the chitosan films at the individual electrode addresses. Protein G was assembled by immersing the chip in 4 ml of PBS solution containing protein G (0.8 μM) for 1 hr. After rinsing, the chip was incubated with fluorescently-labeled human IgG (0.13 μM) for 1 hr. Again, a progressive increase in intensity is apparent from the fluorescence photomicrograph in FIG. 3(c).

Figure 3:
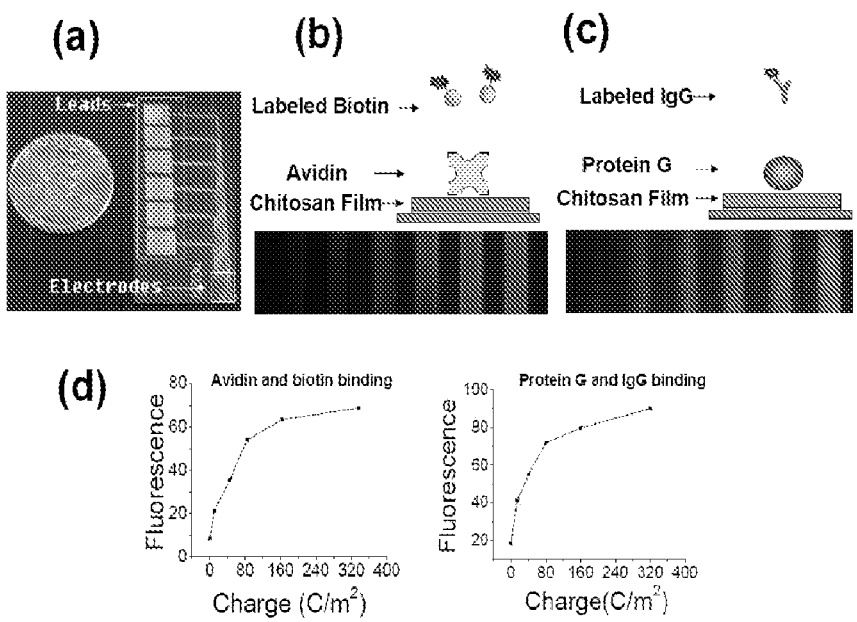
FIG. 3 relates to assembly of target proteins at individual electrode addresses, including: (a) a chip with 6 electrically independent electrode addresses (250 μm wide gold lines spaced 250 μm apart); (b) a schematic of avidin assembly to electrochemically-activated chitosan films and a fluorescence photomicrograph showing binding of labeled biotin; (c) a schematic of Protein G assembly to electrochemically-activated chitosan films and a fluorescence photomicrograph showing binding of labeled human IgG; and (d) a correlation between protein assembly (as determined from image analysis of fluorescence) and the extent of chitosan film activation (as measured by the charge transfer, Q).

Next, the quantitative relationship between protein assembly and electrochemical film activation was established. Protein assembly was quantified using Image-J software (http://rsb.info.nih.gov/ij/) to assess the fluorescence intensities for the images in FIGS. 3(b) and 3(c). The quantitative measure of electrochemical film activation is the amount of charge transferred (Q; C/m$^2$) during anodic activation of the individual electrode addresses:

$$Q = \int i \, dt$$

where i is the current density applied over time t. The plots in FIG. 3(d) show a monotonic increase in fluorescence intensity as a function of the charge transfer for both avidin and Protein G assembly. These results demonstrate that electrochemical activation provides a simple and rapid means to controllably assemble proteins at individual electrode addresses. Importantly, the observed fluorescence in FIG. 3 is a measure of the proteins' functional activity (i.e., to bind either biotin or IgGs).

Figure 12:
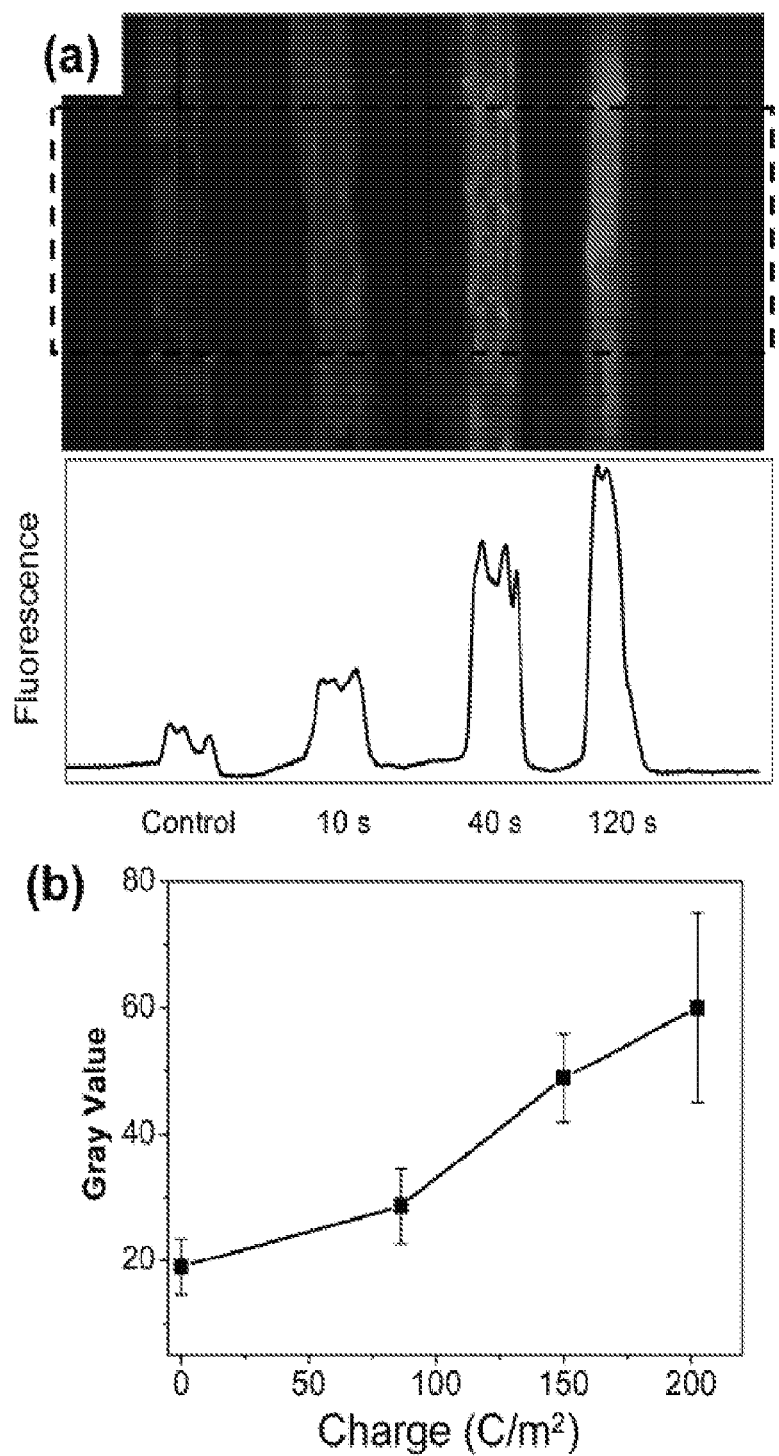
FIG. 12 relates to electrochemical protein conjugation onto chitosan-coated wires. (a) Fluorescence images and image analysis indicate a progressive increase in the conjugation of red fluorescent protein (RFP) with anodic activation time. Electrochemical conjugation was achieved by immersing chitosan-coated wires in a 3 µM RFP solution (0.1 M phosphate, 0.1 M NaCl, pH 7.4) and applying a 0.9 V anodic voltage. The control is a chitosan-coated wire that was immersed in the same RFP solution for 120 s (no voltage applied). (b) Correlation between RFP assembly (as determined from image analysis of fluorescence) and the extent of chitosan film activation (as measured by the total charge transferred).

Although the mechanism of anodic activation of chitosan has not been definitively established, the working hypothesis is that a reactive mediator (possibly hypochlorite OCl$^-$) is electrochemically generated at the anode, and this mediator reacts with the chitosan film to generate reactive substituents (possibly aldehydes) along chitosan's backbone. Experimentally, chitosan-coated gold wires were immersed in 1 mL of phosphate buffer (0.1 M, pH 7.4) containing both NaCl (0.1 M) and the model protein red fluorescent protein (RFP; 3 µM), and ananodic voltage of 0.9 V was applied for varying times. The fluorescence images and image analysis in FIG. 12(a) show a progressive increase in fluorescence with anodic activation time suggesting RFP can be controllably assembled onto the chitosan-coated gold wire. Importantly, the observed fluorescence indicates that RFP's native structure is preserved upon electrochemical conjugation, which indicates that this protein assembly approach is sufficiently mild to prevent (or limit) protein denaturation.

A quantitative analysis of electrochemical RFP conjugation to the chitosan-coated wire is shown in FIG. 12(b). FIG. 12(b) indicates a trend of increasing fluorescence with charge transfer, which has been previously observed with planar electrodes. (Shi, X. -W., et al. *Adv.Mater.* 2009, 21, 984-988.) It should be noted that the correlation between fluorescence and Q is considerably less scattered for the case of planar electrodes than for the gold wires in FIG. 12(b), presumably because of the ease of focusing on planar surfaces during microscopic imaging.

In addition to quantitatively assembling a single protein at the electrode addresses, the quantitative assembly of two different proteins at the electrode addresses was demonstrated. As illustrated in the schematic representation in FIG. 4(a), two model proteins Green Fluorescent Protein (GFP) and Red Fluorescent Protein (RFP) were assembled. Chitosan was first electrodeposited on all 6 addresses of the chip in FIG. 3(a). Next, the chitosan films on the 3 left-most electrodes were anodically activated by biasing them at 0.9 V for varying times (to control Q) while the chip was immersed in a phosphate buffer containing NaCl. After activating these three left electrodes, the chip was contacted with a PBS solution containing GFP (0.6 µM) for 1 hr. After assembling GFP onto the left three electrodes, the chip was washed with PBS containing tween (0.1%) and then immersed in a PBS solution containing bovine serum albumin (BSA, 5%) for 2 hr to block any residual oxidized substituents on the chitosan film. To assemble the second protein, the 3 right-most electrodes were electrochemically activated, and RFP was assembled using the same conditions described for GFP assembly.

Figure 4:
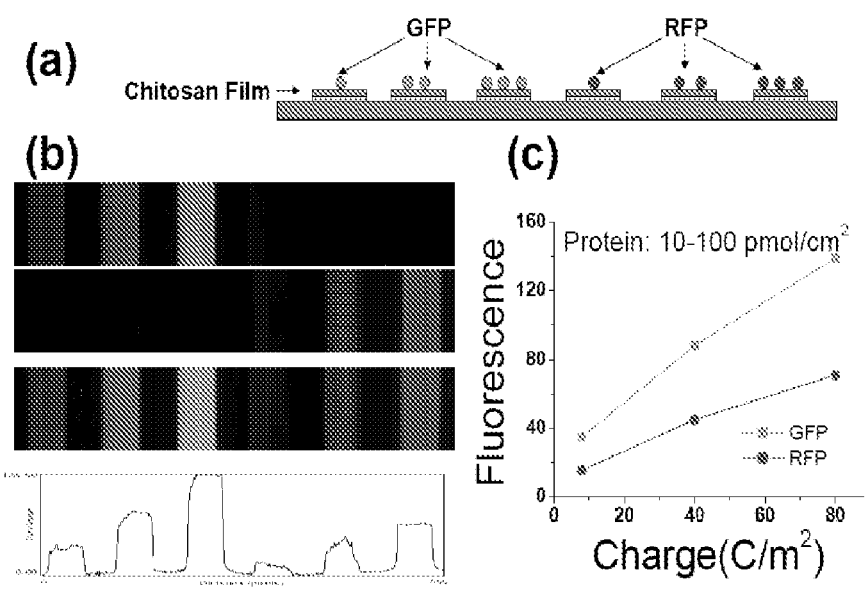
FIG. 4 relates to multiplex protein assembly, including: (a) a schematic illustration of the assembly of Green Florescent Protein (GFP) on the left-most electrodes and Red Florescent Protein (RFP) on the right-most electrodes; (b) a fluorescence photomicrograph of the two proteins assembled on the chip, wherein the top two images were obtained using a single filter while the bottom image is a composite using both red and green filters, with image analysis performed for the composite image; and (c) plots of fluorescence intensity versus charge transfer (Q) for assembly of the two proteins, with an independent calibration indicating that the assembled protein is on the order of 10-100 pmol/cm$^2$.

The upper two images in FIG. 4(b) show fluorescence photomicrographs using an individual green or red filter. These images indicate that GFP is selectively assembled on the left 3 electrode addresses while RFP is selectively assembled on the right 3 addresses. Little non-specific binding is observed in these images. At the bottom of FIG. 4(b) is a composite image using both filters and the analysis of this fluorescence photomicrograph. FIG. 4(c) shows a plot of the fluorescence intensity vs. charge transfer (Q) for assembly of these two proteins. Since relatively small Q values were tested, the assembly of each protein was nearly linear with Q. These results demonstrated the controlled assembly of two proteins in response to localized electrical signals. This protein assembly method can be extended to the sequential assembly of multiple proteins. Importantly, the observed fluorescence in FIG. 4 indicates the native structures of RFP and GFP are retained upon assembly to the activated chitosan films.

To provide a quantitative estimate of the amount of protein assembled onto the activated chitosan films, a standard curve by spotting known amounts of GFP and RFP onto a chitosan-coated electrode was generated and the fluorescence was analyzed. Based on this method, it is estimated that protein assembly onto activated chitosan chips is on the order of 10-100 pmole/$cm^2$. This level of assembly indicates that protein assembly is comparable to, or greater than, monolayer coverage.

The invention therefore provides in various embodiments, devices with varying numbers of proteins at varying electrode addresses. As exemplified, a single protein may be assembled at all electrode addresses, or multiple proteins may be assembled at multiple electrode addresses. Therefore the number of types of assembled proteins ranges from a single protein assembled on all electrode addresses to a different protein assembled at each electrode.

The foregoing results demonstrate that electrode-imposed electrical signals are usefully enlisted for the spatially-selective and quantitatively-controlled assembly of proteins. Specifically, cathodic signals are employed for the electrodeposition of stimuli-responsive aminopolysaccharide chitosan, while anodic signals are employed to selectively activate the chitosan film for protein conjugation. Such on-demand protein assembly is suitably performed from aqueous solution using mild conditions that preserve the proteins' native structure and biological function. This assembly approach is simple, safe and inexpensive, since no reactive reagents are required and the oxidative mediator is electrochemically-generated from NaCl. This assembly approach is usefully employed for the sequential assembly of proteins at individual electrode addresses. These results further demonstrate that chitosan possesses a unique set of properties that facilitate the integration of biological components into electronic devices.

Electrochemical Transduction

Figure 9:
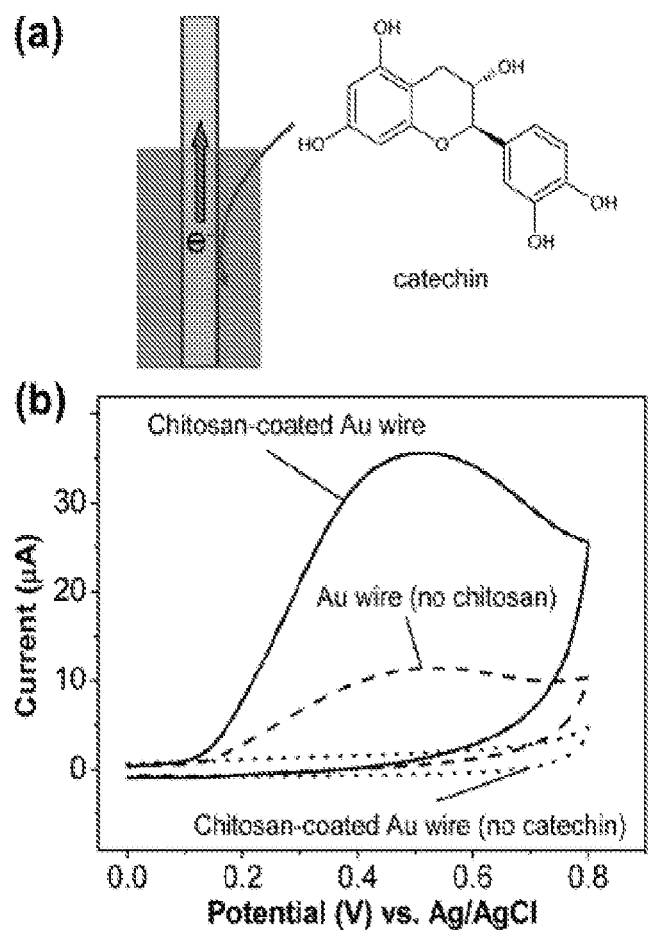
FIG. 9 relates to electrochemical transduction with chitosan-coated wire. (a) Schematic illustrating that phenol (i.e., catechin) can be electrochemically oxidized to generate a detectable electrical signal (current). (b) Cyclic voltammograms (CVs) for a 2 mM catechin solution (0.1 M phosphate buffer, pH) 7.4) show that chitosan-coated gold wire has a strong anodic peak. A smaller anodic peak is observed for an uncoated gold wire in the presence of 2 mM catechin. A control is a chitosan-coated gold wire immersed in buffer (without catechin). Scan rate) 0.1 V/s.

Previous studies demonstrated that chitosan films are permeable to small molecules and that electrochemically active phenols (e.g., food phenols) can be anodically oxidized by chitosan-coated planar electrodes. (Wu, L. Q., et al. *Adv. Funct. Mater.* 2005, 15, 189-195; Wu, L. Q., et al. *Adv.Funct. .Mater.*2006, 16, 1967-1974; Liu, Y., et al. *Langmuir* 2008, 24, 7223-31.) To extend these observations, chitosan was electrodeposited onto gold wires (12.6 $A/m^2$ for 45 s) and these chitosan-coated wires were used to detect the presence of the antioxidant phenol, catechin, as illustrated in FIG. 9(a) and in Example 8. It can be seen that chitosan-coated gold wires immersed in a buffered solution containing catechin demonstrated a strong peak at the anodic potential of 0.5 V for the chitosan-coated wire.

Figure 10:
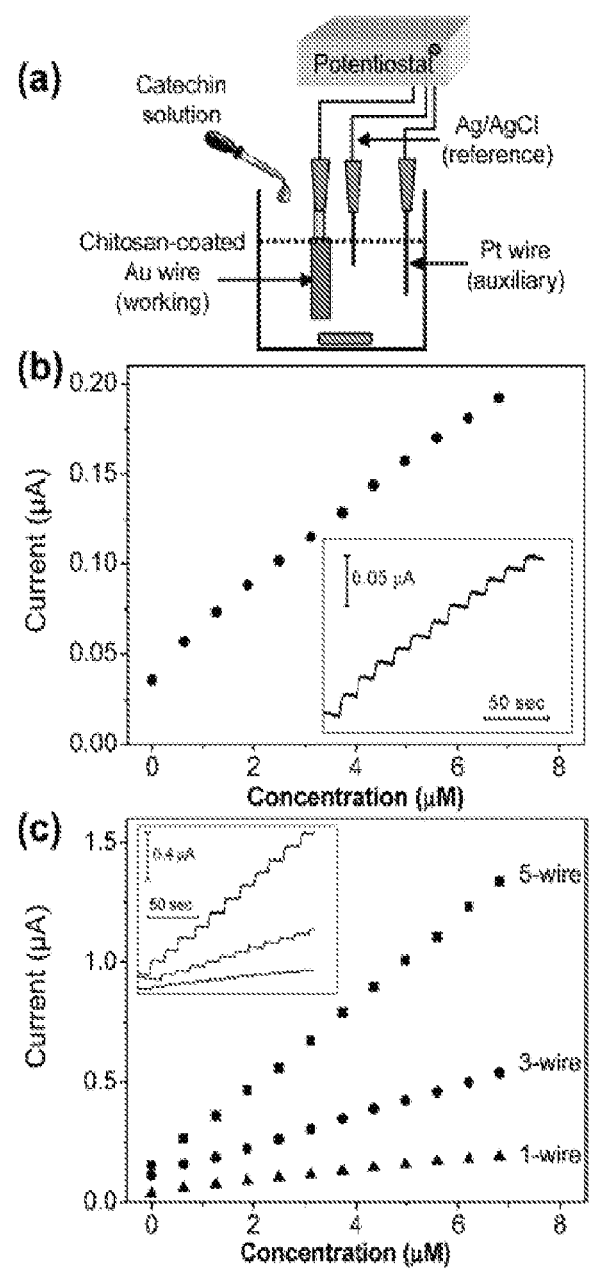
FIG. 10 relates to quantitative analysis of catechin with chitosan-coated wires. (a) Schematic of the i-t(current vs time) measurements using a standard three-electrode configuration. Electrodes were immersed in a buffered solution (0.1 M phosphate, pH 7.4), and the working electrode was biased to 0.5 V. (b) Correlation between the current and catechin level. Inset shows current steps upon sequential additions of 0.6 µM catechin. (c) Sensitivity of electrochemical detection of catechin is increased by increasing the number of chitosan-coated wires.

Additionally, the ability of the chitosan-coated wires to perform quantitative analysis was examined by the step-wise addition of aliquots of catechin, as summarized in Example 9. Increased concentration led to increased measured current, as illustrated in FIGS. 10(a) and 10(b).

Furthermore the effect of an increase in the number of chitosan-coated wires was examined with regard to sensitivity of chemical detection, as summarized in Example 10. The results of Example 10, as illustrated in FIG. 10(c) indicate that the sensitivity of electrochemical detection can be enhanced by simply increasing the total electrode surface area of the chitosan-coated wires (e.g., increasing the number or increasing the length) used for analysis.

One of the advantages of chitosan-coated electrodes for phenol detection is the opportunity for bimodal sensing (electrical plus optical). Specifically, anodically oxidized phenols are reactive and rapidly react with the chitosan film to alter the film's optical properties. (Wu, L. Q., et al. *Adv. Funct. Mater.* 2005, 15, 189-195; Liu, Y., et al. *Langmuir* 2008, 24, 7223-31.) Previous studies with chitosan coated planar electrodes demonstrated that the optical signal (UV-visible absorbance) is linearly correlated with the electrical signal (charge transferred, Q). Thus, optical signals provide an additional observable that adds redundancy to detection. For the case of catechin, anodic oxidation products react with chitosan to generate a fluorescent product. (Wu, L. Q., et al. *Adv. Funct. Mater.* 2005, 15, 189-195.) Demonstration of this behavior for the wire format was provided by the experiment summarized as Example 11 below.

The previous results indicate that chitosan electrodeposition and electrochemical conjugation allow proteins to be simply and rapidly assembled on to conducting wires. In Example 12 the ability of the system or device of the invention to transduce enzyme-substrate recognition into an electrical signal was examined by assembly of an enzyme on the chitosan-coated gold wires. It was demonstrated that biofunctionalized chitosan-coated wires can transduce biorecognition into electrical signals.

Specifically, the common biosensing enzyme glucose oxidase (GOx) was used as the model for biologically based electrochemical transduction. GOx catalyzes the reaction (Lu, Y., et al. *Bioelectrochemistry* 2007, 71, 211-6; Du, Y., et al. *Bioelectrochemistry* 2007, 70, 342-7; Zhou, Q., et al. *J. Phys. Chem.* 2007, 111, 11276-84):

$$glucose + O_2 \rightarrow gluconic\ acid + H_2O_2$$

The hydrogen peroxide generated by this enzymatic reaction can be anodically oxidized to generate an electrical signal by the reaction (Xi, F., et al. *Biosens. Bioelectron.* 2008, 24, 29-34):

$$H_2O_2 \rightarrow O_2 + 2H^+ + 2e^-$$

As set forth in Example 12, two different methods were examined for assembling GOx onto the gold wire. The first approach, pioneered by Chen et al. for GOx assembly onto planar electrodes is to codeposit GOx with the chitosan (Luo, X. L., et al. *Anal. Biochem.* 2004, 334, 284-289; Bai, Y. H., et al. *Electrochem. Commun.* 2007, 9, 2611-2616; Luo, X. L., et al. *Biosens.Bioelectron.*2005, 21, 190-196.). The second assembly approach was the electrochemical conjugation of GOx to chitosan-coated wires.

Figure 14:
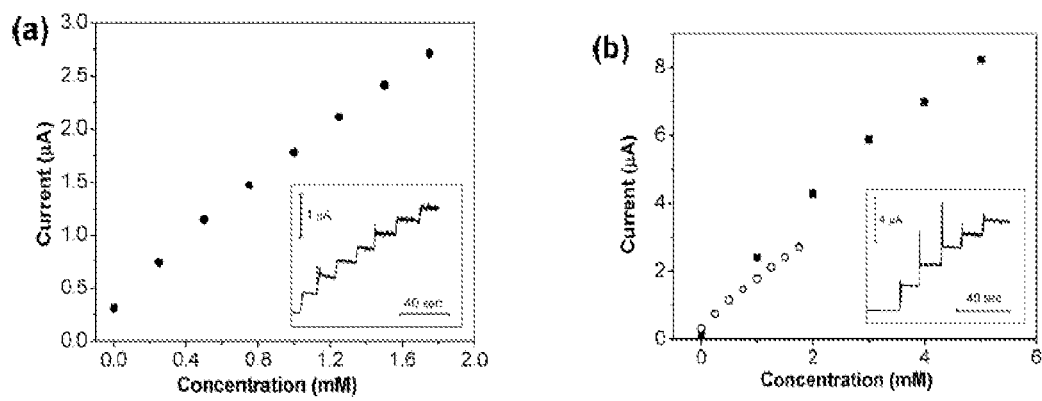
FIG. 14 relates to quantitative signal transduction from GOx-functionalized chitosan-coated wires. GOx was electrochemically conjugated to chitosan-coated wire and glucose was detected amperometrically (as in FIG. 10). (a) Standard curve between anodic current and glucose concentration at low concentrations (each aliquot increased the glucose concentration by 0.25 mM). (b) Standard curve over a broader concentration range using a different GOx-functionalized chitosancoated wire (each aliquot increased the glucose concentration by 1.0 mM). Note the data in (a) are reproduced in (b), open circles.

Results shown in Example 12 with the GOx-functionalized chitosan-coated wires demonstrate that the biological generation of electrochemically active species can be quantitatively transduced into convenient electrical signals. Consistent with other "first generation" GOx based glucose sensors, the chitosan-coated wire offers submillimolar limits-of-detection, while analysis of the data in FIG. 14 indicates an apparent Km of 10 mM, which is also consistent with GOx-based biosensors (Kang, X. H., et al. *Anal.Biochem.*2007, 369, 71-79; Manesh, K. M., et al. *Biosens.Bioelectron.*2008, 23, 771-779; Tan, X. C., et al. *Anal.Bioanal.Chem.*2005, 381, 500-507; Wu, B. Y., et al. *Biosens.Bioelectron.*2007, 22, 838-844; Zou, Y. J., et al. *Biosens.Bio-electron.*2008, 23, 1010-1016.). Additional results with GOx-functionalized wires for biosensing are provided as Supporting Information, which can be accessed at hyper text transfer protocol internet address: pubs.acs.org. In order to standardize fabrication methods to ensure wire-to-wire reproducibility and to overcome problems of interference mediators have been used in later generations of GOx-based glucose sensors (Castillo, J., et al. *Sens. Actuators,* 2004, 102, 179-194; Heller, A., et al. *Chem.Rev.*2008, 108, 2482-2505; Wang, J., et al. *Chem.Rev.*2008, 108, 814-825.).

It is shown herein that chitosan is a unique material that "recognizes" cathodic signals and responds by electrodepositing as a stable film. Further, anodic signals can activate chitosan for protein assembly, thus allowing chitosan to be biofunctionalized. These capabilities of chitosan facilitate the coupling of the molecular recognition properties of proteins (e.g., glucose oxidase) with the transduction capabilities of metals for electrical signaling. Importantly, electrodeposition and electrochemical protein conjugation are achieved rapidly without the need for reactive reagents or complex activation and protection steps. Thus, the preparation of biofunctionalized chitosan-coated wires is simple, safe, and inexpensive.

Chitosan-coated wires are an interesting platform that can be viewed as either conducting fibers or functionalized wires. This platform is particularly attractive for biosensing applications outside the laboratory for two general reasons: First, electrochemical detection can be performed in simple, robust, and inexpensive systems that can be miniaturized as hand held or wearable devices; and second, fibers (or wires) of different functionalities can be prepared and assembled on a "mix-and-match" basis to tailor the biosensing capabilities to the specific needs. Thus, assemblies of chitosan-coated wires may allow multiplexed biosensing in the field while accessing the power of electronics for signal processing and wireless communication.

In sum, the above results demonstrate that chitosan-coated wires can transduce chemical information of their environment into convenient electrical signals. As demonstrated in Examples 9-11, the chitosan-coated wires provide a convenient electrical signal for detection and quantification. Using the exemplary protein catechin, the chitosan-coated wire provided an additional optical (i.e., fluorescence) signal that can be used to provide confirmatory information. It should be noted that while the electrical signal is an instantaneous measure, the fluorescence is a cumulative measure of protein.

Devices of the invention may be used in formation of filaments or fibers or in the generation of textiles or garments comprising such devices. The devices of the invention may be utilized as wearable instruments or smart textiles. In one embodiment the wearable instruments or smart textiles are utilized as a sensor to detect condition of the wearer or user. Conditions sensed by the sensor may include, but are not limited to a condition of wearer such as vital signs, temperature, heart rate, blood pressure, respiration rate, etc. and/or ambient conditions such as temperature, pressure, light, etc. or other environmental stimuli, such as those from mechanical, thermal, chemical, electrical, magnetic or other sources. Smart textiles are capable of a range of functions, such as sensing, detecting, initiating, reacting, regulating and communicating.

In another embodiment the devices of the invention are used in hand-held devices for applications such as point-of-care detection and diagnosis of disease, assessment of environmental samples, and food safety assessment.

The advantages and features of the invention are further illustrated with reference to the following examples, which are not to be construed as in any way limiting the scope of the invention but rather as illustrative of specific embodiments of the invention in particular applications thereof.

The following examples use materials obtained as follows:

The following materials were purchased from Sigma-Aldrich: chitosan from crab shells (85% deacetylation and 200 kDa, as reported by the supplier); atto 565 labeled biotin; human IgG labeled with fluorescein; bovine serum albumin (BSA); Tween 20; Goldwire (99.9+%, 0.25 mm diameter), (+)-catechinhydrate, D-(+)-glucose (99.5%), and glucose oxidase (GOx from *Aspergillusniger;* 136 kU/gm).

Avidin D was purchased from Vector Laboratories. Texas Red labeled BSA was purchased from Invitrogen.

Platinum/silver wires (99.95%) were purchased from Surepure Chemetals Inc.

NHS-Fluorescein was purchased from Pierce.

Nonfat dry milk was purchased from Lab Scientific.

Red fluorescent protein (RFP), green fluorescent protein (GFP) and Protein G were expressed from *E. coli* and purified using standard methods (X W Shi, et al, *Biomacromolecules* 2008, 9, 14-17). Silicon wafers were patterned using standard photolithographic methods (L -Q. Wu, et al, *Langmuir* 2003, 19, 519).

EXAMPLE 1

Chitosan Electrodeposition

A chitosan solution (0.9 w/v %) was used for chitosan electrodeposition. This solution was prepared by adding chitosan to 1% HCl, mixing overnight, and filtering using a vacuum filter to remove undissolved particles. The pH of this chitosan solution was then adjusted to 5.6 using 1 M NaOH.

Chitosan films were electrodeposited on two adjacent electrodes of the chip in FIG. 2(b). Chemical analysis of electrochemically-activated chitosan films was performed using X-ray Photoelectron Spectroscopy (XPS). One film served as the control, while the other was anodically activated. XPS analysis was performed on a Kratos Axis 165 using Al Ka (1486.7 eV) radiation at 300 W (http://www.chem.umd.edu/facility/xps.php). The system was operated in the hybrid mode, survey spectra were collected with a pass energy of 160 eV and high resolution spectra at a pass energy of 20 eV. The working pressure of the instrument was at $1\times10^{-8}$ Torr or better throughout data collection. All spectra were calibrated to the hydrocarbon peak at 284.6 eV. Peak fitting was carried out after the application of a Shirley background, peaks with a 60% Gaussian, 40% Lorentzian line shape were used to fit the O 1 s, C 1 s and N 1 s regions with FWHM values equal to 1.90, 1.50, and 1.75 eV respectively.

EXAMPLE 2

Protein Assembly

Protein assembly was performed using three steps. First, chitosan was electrodeposited by partially immersing the patterned chip into the chitosan solution (0.9%, pH 5.6), applying a cathodic voltage to achieve a constant current density of 4 $A/m^2$ for 15 sec. After deposition, the chips were rinsed with water. The second step was to electrochemically activate the deposited chitosan film. Activation was performed by partially immersing the chips in a 0.1 M phosphate buffer (pH 7) containing 0.1 M NaCl, connecting the chitosan-coated electrode to serve as the working electrode in a 3-electrode system, and biasing the chitosan-coated electrode to an anodic voltage of 0.9 V to achieve a specific charge transfer (Q). The three-electrode system (CHI627C electrochemical analyzer, CH Instruments, Inc.) employed Ag/AgCl as the reference electrode and a Pt wire as the counter electrode. For the third step, protein conjugation to the activated films, the chips were washed with 0.1 M PBS, and then immersed in a solution containing the target protein and incubated for 1 hr (no power was supplied during this third step). Protein assembly was observed using fluorescence microscopy (Leica MZFL III) and the images were analyzed using ImageJ software (http://rsb.info.nih.gov/ij/).

EXAMPLE 3

NaCl is Required for Anodic Activation

Figure 5:
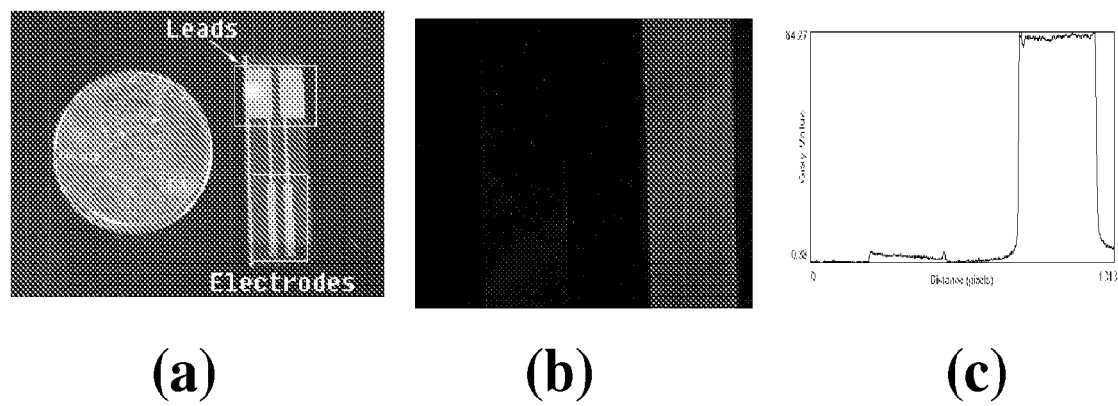
FIG. 5 relates to NaCl being required for chitosan film activation, with (a) a chip with 2 electrically-independent electrode addresses; (b) protein assembly onto electrodeposited chitosan films, with the control chitosan film on the left electrode anodically activated in 0.1 M phosphate buffer (pH=7.0), while chitosan film on the right electrode was activated in 0.1 M phosphate buffer containing 0.1 M NaCl, and after activation, the chip was immersed in a solution containing the model Red Fluorescent Protein (RFP), and (c) analysis of the image of (b).

FIG. 5 compares protein binding to chitosan films activated in 0.1 M phosphate buffer (pH=7.0) with and without NaCl. Initially, chitosan films were electrodeposited on both electrodes of the patterned chip shown in FIG. 5(a). After washing with water, the right electrode was connected to a power supply and served as the working electrode in a 3-electrode system (Ag/AgCl as a reference and Pt wire as a counter electrode) and the electrodes were immersed in 0.1 M phosphate buffer with 0.1 M NaCl. In this example, a somewhat different procedure was used to activate the chitosan film. Specifically, the potential of the underlying electrode was linearly increased from 0 to 1.5 V at rate of 100 $mV\text{-}s^{-1}$. This linear increase in voltage was repeated a total of 5 times. The chitosan film on the left electrode served as a control in which the same "activation" procedure was performed in 0.1 M phosphate buffer lacking NaCl. After washing with 0.1 M PBS buffer for 20 min, the chip was immersed in a solution containing red fluorescent protein (RFP; 0.6 µM) for 1 hr. FIG. 5(b) shows the fluorescence photomicrograph from a Leica fluorescence microscope (MZFL III) and analysis by Image J software (http://rsb.info.nih.gov/ij/). Substantial fluorescence was observed on the right electrode on which the chitosan film had been anodically oxidized in the presence of NaCl, while little fluorescence was observed on control chitosan film on the left electrode. These results indicate that anodic activation of chitosan requires the presence of NaCl and suggests that oxidized NaCl species (e.g., HOCl or $OCl^-$) may serve as the mediator for film activation.

EXAMPLE 4

Chitosan is Required for Electrochemical Protein Assembly

Figure 6:
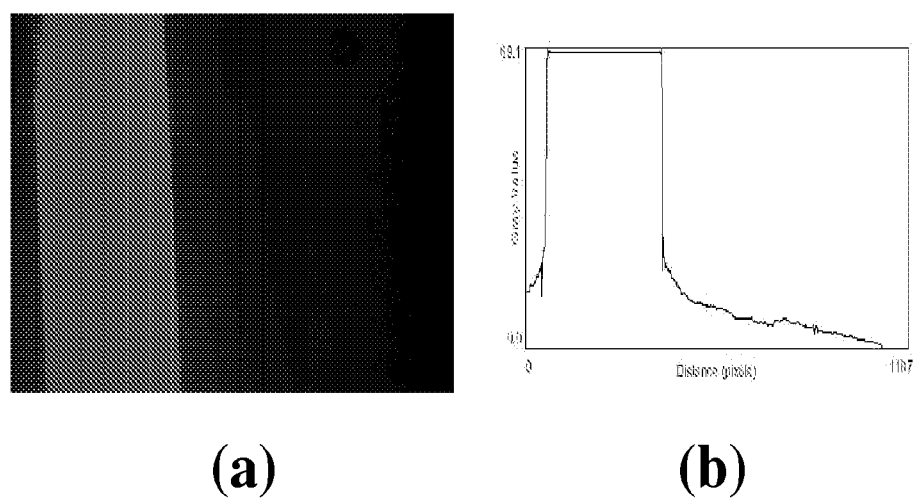
FIG. 6 relates to chitosan being required for electrochemical protein assembly, including: (a) chitosan electrodeposited on the left electrode of the chip of FIG. 5(a) while the right electrode was untreated, and after anodic oxidation of both electrodes (0.9 V, Q=80 C/m$^2$), the chip was immersed in a solution of labeled bovine serum albumin (BSA), with the fluorescence photomicrograph indicating that the labeled BSA was assembled on the chitosan-coated (left) electrode but not onto the bare gold electrode; and (b) analysis of the image in FIG. 6(a).

FIG. 6 compares protein assembly to an activated chitosan film with assembly to an uncoated (bare) gold electrode. In this example, the chip in FIG. 5(a) was used, chitosan was electrodeposited on the left electrode, and the right electrode was uncoated. During anodic activation, both electrodes were biased to an anodic potential (0.9 V) and the charge transfer was 80 $C/m^2$. After washing the chip with PBS buffer for 20 minutes, the chip was immersed in fluorescently-labeled bovine serum albumin (Texas red-BSA; 0.5 µM) for 1 hr. After washing the chip with PBS containing 0.1% Tween, the chip was examined using fluorescence microscopy. The images in FIG. 6 show red fluorescence on the chitosan film on the left electrode while no fluorescence was observed on the gold electrode that lacked the chitosan film. This result indicates that anodic treatment activates the chitosan film for subsequent protein assembly, while the gold electrode was not activated by biasing to anodic conditions.

EXAMPLE 5

Oxidized Substituents of Chitosan are Responsible for Protein Assembly

Figure 7:
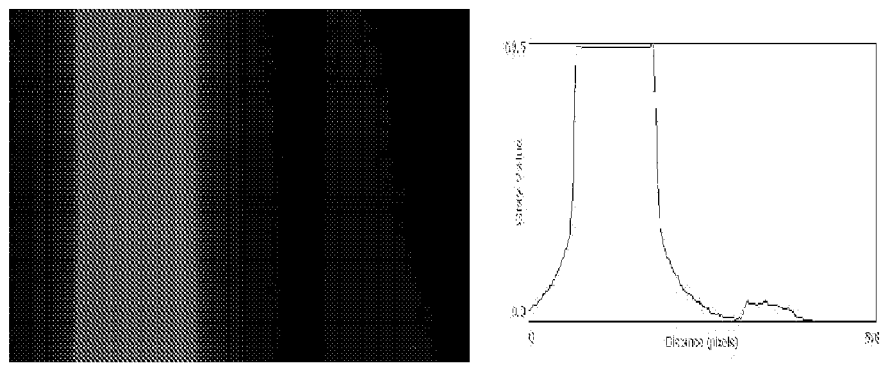
FIG. 7 relates to activated chitosan films, as "de-activated" by treatment with a reducing agent, wherein chitosan was electrodeposited on both electrodes of the chip of FIG. 5(a), the right electrode anodically activated (0.9 V, Q=80 C/m$^2$) and thereafter was treated with NaBH$_4$ (0.2 mg/ml) for 1 hr, following which the left electrode was anodically activated, and the chip was immersed in a solution containing labeled BSA, the fluorescence photomicrograph indicating that treatment by the reducing agent disrupts protein assembly; and (b) analysis of the image of FIG. 7(a).

FIG. 7 compares protein assembly to an activated chitosan film, with and without treatment with a chemical reducing agent. In this example, chitosan was electrodeposited to both electrodes of the chip shown in FIG. 5(a). The chitosan film on the right electrode was activated by biasing the underlying electrode to an anodic potential (0.9 V to a charge transfer of 80 $C/m^2$). Next, the chip was contacted with the reducing agent $NaBH_4$ (0.2 mg/ml) for 1 hr. After washing the chip with PBS, the chitosan on the left electrode was anodically activated by biasing its underlying electrode (0.9 V, Q=80 $C/m^2$). After washing the chip with PBS buffer for 20 minutes, the chip was contacted with a solution of the labeled BSA (0.5 μM) for 1 hr. FIG. 7 shows strong fluorescence on the left chitosan film, while low levels of fluorescence were observed on the right film. This result indicated that the activated chitosan film was "de-activated" by treatment with a reducing agent, and that anodic activation leads to oxidation of the chitosan, and the oxidized substituents (aldehydes) are capable of reacting with proteins.

EXAMPLE 6

Second Example of Chitosan Electrodeposition

A chitosan solution (1 w/w %) was prepared by adding chitosan flakes to water and slowly adding 1% HCl to dissolve the polysaccharide (final pH 5.6). After mixing overnight, the solution is filtered using a vacuum filter to remove undissolved particles. Fluorescein-labeled chitosan was prepared from a chitosan film. The film was prepared by pouring a chitosan solution into a Petri dish, drying overnight at 45° C., neutralizing the film with 0.1 M NaOH for 30 min, and then washing the film with water. The film was labeled by placing it in 10 mL of water, adding NHS-fluorescein (5 mg/mL in DMSO) to a final concentration of 0.5 μg/mL, and incubating at room temperature for 30 min. After labeling, the labeled chitosan film was washed with copious amounts of water. The labeled chitosan film was then dissolved by adding small additions of 1% HCl to achieve a pH between 5 and 6.

Electrodeposition and codeposition were performed using 1 cm gold wires. Before use, the gold wires were cleaned by immersing in piranha solution (7:3 concentrated $H_2SO_4$: 30% $H_2O_2$) for 30 min. For deposition, the gold wires were immersed in a solution of chitosan (for code position studies, the chitosan solution also contained 680 U/mLGOx). An alligator clip was used to connect the wire to a DC power supply (2400 Sourcemeter, Keithley) and the gold wire was biased to serve as the cathode (negative electrode) while a platinum wire served as anode. Electrodeposition was performed at a constant current density of 12.6 A/m² for 15-90 s (typical voltages of 2-3 V). After electrodeposition, the wire was immediately removed from the deposition solution, briefly rinsed with water, and dried in air before use.

EXAMPLE 7

Second Example of Protein Assembly

Electrochemical protein conjugation to chitosan-coated wire was achieved using a procedure adapted from a previous study (Shi, X. W., et al. *Adv.Mater.* 2009, 21, 984-988.). First, chitosan was electrodeposited by immersing 1 cm of gold wire into the chitosan solution and applying a cathodic voltage at a constant current density of 12.6 A/m² for 20 s. After deposition, the wires were rinsed with water. The second step was to electrochemically conjugate protein (either RFP or GOx). Conjugation was performed by (i) immersing the chitosan-coated wire in a solution (0.1 M phosphate buffer with 0.1 M NaCl, pH 7.4) containing protein, (ii) connecting the chitosan-coated electrode to serve as the working electrode in a three-electrode system, and (iii) biasing the chitosan-coated electrode to ananodic voltage of 0.9 V (vs Ag/AgCl) for a specific time (typically 1 min). The protein-functionalized wires were then washed three times (10 min each) in 0.1 MPBS (containing 0.05% Tween 20) to remove nonspecifically bound protein.

The wires were examined using a Leica fluorescence microscope (MZFLIII). To observe fluorescence associated with fluorescein-labeled chitosan, a GFP plus filter with excitation filter at 480/40 nm and emission filter at 510 was used. The fluorescence associated with the catechin-modified chitosan was observed using a GFP filter with an excitation filter at 425/60 nm and an emission filter at 480 was used. To observe red fluorescence (e.g., for RFP), a Leica 41004 TXRD filter was used with excitation filter at 560/55 nm and an emission barrier at 645/75 nm. Fluorescence micrographs were obtained using a digital camera (spot 32, Diagnostic Instrument) connected to the fluorescence microscope and the images were analyzed using ImageJ software (hyper text transfer protocol internet address: //rsb.info.nih.gov/ij/).

EXAMPLE 8

Detection of the Presence of Catechin

A chitosan-coated wire was immersed in a buffered solution containing catechin (2 mM, pH 7.4) and a cyclic voltammogram (CV) was generated. FIG. 9(b) shows a strong peak at the anodic potential of 0.5 V for the chitosan-coated wire. A CV for a control chitosan-coated wire immersed in a catechin-free solution shows no anodic peak. An uncoated gold wire immersed in the catechin-containing solution was tested as a second control. The CV for this uncoated wire also shows a peak current near 0.5 V, consistent with catechin's oxidation; however, the peak current for this control is considerably less than that observed for the chitosan-coated wire. The higher sensitivity of chitosan-coated electrodes has been previously observed and is presumably due to a preconcentration effect (Liu, Y., et al. *Langmuir* 2008, 24, 7223-31.).

Electrochemical measurements such as cyclic voltammetry (CV), amperometric current versus time measurements, and chronocoulometry were carried out with a CHI627C Electrochemical Analyzer (CH Instruments, Inc., Austin, Tex.). Measurements were performed using a standard three-electrode configuration and the specific experimental conditions provided herein.

EXAMPLE 9

Quantitative Analysis of Phenol Levels

Chitosan-coated wires were immersed in a buffered solution (0.1 M phosphate, pH 7.4), biased to 0.5 V, and aliquots of catechin were sequentially added to increase the concentration by 0.6 μM, as illustrated in FIG. 10(a). The inset to FIG. 10(b) shows that after each catechin addition, a step-change in current is observed. The plot in FIG. 10(b) shows a strong correlation between the current and the catechin level. The micromolar limit of detection observed in FIG. 10(b) is considerably larger than the typical catechin concentrations found in wines and tea. (Dalluge, J. J., et al. *J.Chromatogr.*, 2000, 881, 411-424; Arts, I.C.W., et al. *J. Agric. Food Chem.* 2000, 48, 1752-1757.)

EXAMPLE 10

Sensitivity of Electrochemical Detection

In Example 10 it was examined how the sensitivity of electrochemical detection could be increased by simply increasing the number of chitosan-coated wires used for detection (i.e., by increasing the electrode surface area).

The inset to FIG. 10(c) shows the step increase in current observed for each catechin addition for systems containing one, three, or five chitosan coated wires. The plot in FIG. 10(c) shows an early linear correlation between the observed current and the catechin concentration for each of these experimental systems. As expected, the slopes of these plots (i.e., the sensitivity) increase in the order 0.023, 0.062, and 0.17 μA/μM for the one-, three-, and five-wire systems, respectively.

EXAMPLE 11

Fluorescent Detection of Catechin

Figure 11:
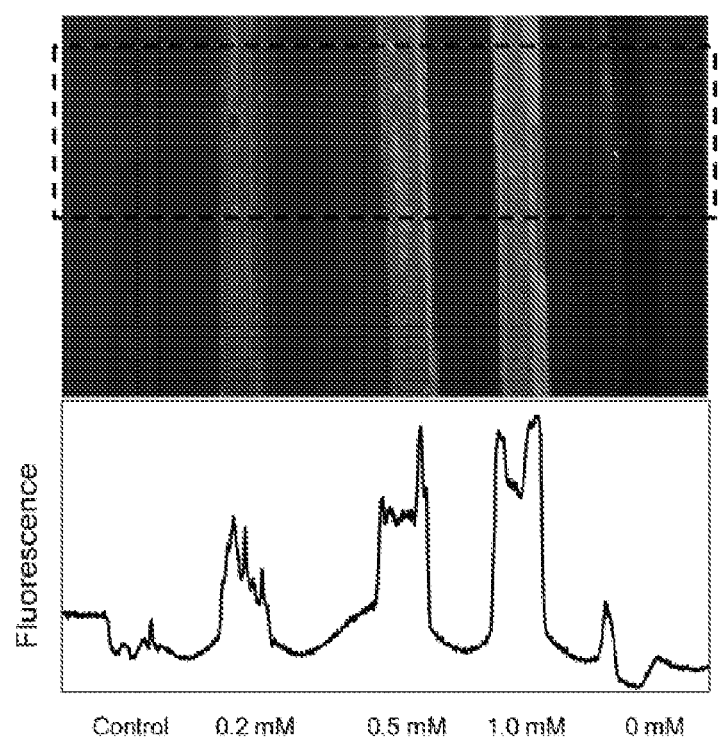
FIG. 11 relates to catechin oxidation confers fluorescence to chitosan-coated gold wires. Fluorescence images and image analysis of chitosancoated wires show a progressive increase in fluorescence with catechin level in the solution. The wires were immersed in solutions containing different concentrations of catechin (0, 0.2, 0.5, and 1.0 mM) and biased to an anodic voltage of 0.5 V for 2 s. The control is a chitosan-coated wire that was immersed in a 1.0 mM catechin for 2 s in the absence of an applied voltage.

Chitosan-coated gold wires were immersed in solutions containing differing concentrations of catechin and applied a positive (i.e., anodic) voltage of 0.5 V for 2 s. After this reaction, the wires were rinsed and examined using fluorescence microscopy. FIG. 11 shows a progressive increase in fluorescence of the chitosan-coated wires with the catechin levels in the solution. Two controls are shown in FIG. 11. The first control, shown at the left, is for a chitosan-coated wire immersed in a catechin solution (1 mM) for 2 s without applying a voltage. The second control, shown at the right in FIG. 11, is for a chitosan-coated wire immersed in a solution lacking catechin, but biased to 0.5 V for 2 s. Neither control displays significant fluorescence. Also, an uncoated gold wire does not become fluorescent upon catechin oxidation under the same conditions (data not shown).

EXAMPLE 12

Electrochemical Transduction

Codeposition of GOx

Figure 13:
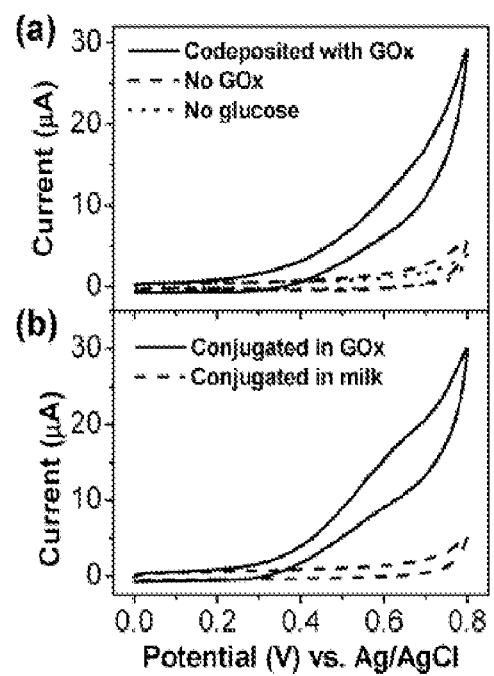
FIG. 13 relates to cyclic voltammograms for chitosan-coated wires functionalized with GOx. (a) Wires biofunctionalized by codeposition show a strong anodic signal in a 2 mM glucose solution. Chitosan and GOx were codeposited from a solution (1% chitosan, 680 U/mL GOx, pH 5.6) at a current density of 12.6 A/m$^2$ for 20 s. (b) Wires biofunctionalized by electrochemical conjugation show a strong anodic signal in a 2 mM glucose solution. GOx was electrochemically conjugated by immersing the chitosan-coated wires in a solution (0.1 M phosphate, 0.1 M NaCl, 680 U/mL GOx, pH 7.4) and applying an anodic voltage of 0.9 V for 60 s. As a control, electrochemical conjugation was performed with nonfat dry milk (5% milk), and the milk-conjugated chitosan-coated wire was tested in the 2 mM glucose solution.

GOx is mixed into the chitosan-containing solution and electrodeposition is performed using this GOx chitosan solution. The electrodeposited chitosan film appears to have a sufficiently fine mesh-size that the codeposited proteins are entrapped within the film's network for some time. GOx was codeposited from a solution (680 U/mL GOx, 1% chitosan, pH5.6) for 20 s at a current density of 12.6 A/m$^2$. After codeposition, the biofunctionalized wire was immersed in a solution containing glucose (2 mM) and a cyclic voltammogram (CV) was generated. FIG. 13($a$) shows a strong anodic signal for the wire with codeposited GOx. Two controls were performed: a chitosan-coated wire lacking GOx that was immersed in the glucose-containing containing solution and a GOx-chitosan-coated wire immersed in a solution lacking glucose. The CVs for these controls show no anodic peaks.

Electrochemical Conjugation of GOx

Chitosan was first electrodeposited onto the wire under cathodic conditions. Then the chitosan-coated wire was immersed in a solution containing buffer (0.1 M phosphate, pH 7.4), NaCl (0.1 M), and GOx (680 U/mL), and the wire was biased to 0.9 V for 60 s. After electrochemical conjugation of GOx, the biofunctionalized wire was immersed in the glucose solution (2 mM) and a CV was generated. FIG. 13($b$) shows a strong anodic signal for this electrochemically conjugated wire. As a control, a chitosan-coated wire was conjugated with milk by performing electrochemical conjugation in a solution containing nonfat dry milk (5%). The CV for this milk-conjugated control wire in the 2 mM glucose solution shows no anodic signal. These initial results indicate that (i) GOx can be assembled onto (or within) the chitosan-coated wire, (ii) GOx retains its biological (i.e., catalytic) function, and (iii) GOx functionalized wires can transduce information of its environment (i.e., the presence of glucose) into electrical signals.

Steady State Current vs. Glucose Concentration

Finally, a standard curve between the steady state current and the glucose concentration for GOx functionalized chitosan-coated wires was generated. When methods described above were used, cathodic signals were used to electrodeposit chitosan onto the gold wire and then anodic signals were used to conjugate GOx to the chitosan-coated wires. These GOx-functionalized wires were then immersed in a buffer (0.1 M phosphate, pH 7.4) and biased to 0.8 V to serve as the working electrode in the three-electrode system. Analogous to the studies with catechin (FIG. 10), aliquots of glucose were then added to the buffer (each aliquot increased the glucose concentration by 0.25 mM). The inset in FIG. 14($a$) shows a step-increase in anodic current was observed after each glucose addition, while the standard curve shows an early linear relationship between anodic current and glucose concentration. In a separate experiment with a different GOx-functionalized chitosan-coated wire, FIG. 14($b$) shows that a similar relationship was observed over a broader range of glucose concentrations.

The foregoing examples demonstrate the utility of the invention for use of electrical signals to effect protein assembly.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A method of forming a bioelectronic device including a protein on an electrically conductive substrate, comprising:
    electrodepositing aminopolysaccharide chitosan on the substrate while applying a cathodic voltage to the substrate, to form an aminopolysaccharide chitosan film thereon;
    applying an anodic voltage to the substrate in the presence of NaCl to activate the aminopolysaccharide chitosan film so that it is reactive with protein; and
    reacting the aminopolysaccharide film, after activation thereof, with the protein, so that the protein assembles on and is coupled to the substrate, thereby forming said bioelectronic device.

2. The method of claim 1, wherein the electrically conductive substrate comprises an electrode on a silicon chip.

3. The method of claim 2, wherein the electrode comprises a gold electrode or a copper electrode.

4. The method of claim 1, wherein the protein is selected from the group consisting of avidin, an immunoglobulin-binding protein, protein G, red fluorescent protein, green fluorescent protein, and glucose oxidase.

5. The method of claim 1, wherein the substrate comprises a multiplexing chip having a multiplicity of electrode addresses, wherein the electrode addresses independently have said protein assembled thereon and coupled thereto.

6. The method of claim 5, wherein said protein comprises at least one biosensor protein species.

7. The method of claim 5, wherein the electrode addresses have different protein species assembled thereon and coupled thereto.

8. The method of claim 7, wherein said different protein species comprise biosensor protein species.

9. The method of claim 7, wherein the different protein species are selected from avidin, an immunoglobulin-binding protein, protein G, red fluorescent protein, green fluorescent protein and glucose oxidase.

10. A method of forming an electrically conductive substrate adapted for assembly of a protein species thereon, said method comprising:
   electrodepositing aminopolysaccharide chitosan on the substrate while applying a cathodic voltage to the substrate sufficient to form an aminopolysaccharide chitosan film thereon; and
   applying an anodic voltage to the substrate in the presence of NaCl to activate the aminopolysaccharide chitosan film so that it is reactive with the protein species.

* * * * *